United States Patent
Jones et al.

(10) Patent No.: US 6,701,327 B1
(45) Date of Patent: Mar. 2, 2004

(54) MERGING NETWORK DATA SETS COMPRISING DATA ACQUIRED BY INTERROGATION OF A NETWORK

(75) Inventors: Paul Robert Jones, Luton (GB); Simon Peter Valentine, Hemel Hempstead (GB); Lee Anthony Walker, Watford (GB); Russell Kennett Bulmer, Hemel Hempstead (GB)

(73) Assignee: 3Com Corporation, Santa Clara, CA (US)

( * ) Notice: Subject to any disclaimer, the term of this patent is extended or adjusted under 35 U.S.C. 154(b) by 0 days.

(21) Appl. No.: 09/447,096

(22) Filed: Nov. 22, 1999

(30) Foreign Application Priority Data

May 11, 1999 (GB) ............................... 9910961
Jul. 20, 1999 (GB) ............................... 9917023

(51) Int. Cl.⁷ ............................... G06F 17/30
(52) U.S. Cl. ............................... 707/200; 707/10
(58) Field of Search ............................... 707/1, 4, 7, 10, 707/100–104.1, 200–203

(56) References Cited

U.S. PATENT DOCUMENTS

| | | | |
|---|---|---|---|
| 4,545,011 A | 10/1985 | Lyon et al. ............... | 364/200 |
| 5,276,789 A | 1/1994 | Besaw et al. ............... | 395/140 |
| 5,689,647 A * | 11/1997 | Miura ............... | 700/2 |
| 5,706,509 A * | 1/1998 | Man-Hak Tso ............... | 707/200 |
| 5,737,319 A | 4/1998 | Croslin et al. ............... | 370/255 |
| 5,798,935 A * | 8/1998 | Doreswamy et al. ............... | 714/700 |
| 5,920,699 A * | 7/1999 | Bare ............... | 709/225 |
| 5,948,055 A * | 9/1999 | Pulsipher et al. ............... | 709/202 |
| 6,003,080 A * | 12/1999 | Ratcliff et al. ............... | 370/400 |
| 6,032,183 A * | 2/2000 | Chen et al. ............... | 707/1 |
| 6,141,567 A * | 10/2000 | Youssefmir et al. ............... | 375/349 |
| 6,167,403 A * | 12/2000 | Whitmire et al. ............... | 707/10 |
| 6,263,278 B1 * | 7/2001 | Nikiel et al. ............... | 340/995 |
| 6,292,801 B1 * | 9/2001 | Campbell et al. ............... | 370/338 |
| 6,338,092 B1 * | 1/2002 | Chao et al. ............... | 707/201 |
| 6,411,997 B1 * | 6/2002 | Dawes et al. ............... | 709/224 |

FOREIGN PATENT DOCUMENTS

| | | | |
|---|---|---|---|
| EP | 0 621 706 A2 | 10/1994 | ............ H04L/12/24 |
| EP | 0 695 100 A2 | 1/1996 | ............ H04Q/3/00 |
| EP | 0 715 435 A2 | 6/1996 | ............ H04L/12/24 |

\* cited by examiner

*Primary Examiner*—Greta Robinson
*Assistant Examiner*—Harold E. Dodds, Jr.
(74) *Attorney, Agent, or Firm*—McDonnell Boehnen Hulbert & Berghoff (57) ABSTRACT

A method for providing a data set relating to a network by merging a first data set relating to the network at a first time and a second data set relating to the network at a s second, later, time, said first data set comprising data acquired by interrogation of the network and other data, and said second data set comprising data acquired by interrogation of the network, said method comprising: comparing the data in the first data set with the second data set, and updating the first data set to include additional data present in the second data to set which is not present in the first data set.

42 Claims, 6 Drawing Sheets

Fig. 1

LEGEND

○ Validated Device

BEFORE INTERROGATION          AFTER INTERROGATION

New Link                    *Fig. 2*

BEFORE INTERROGATION          AFTER INTERROGATION

Link                          Link A & C Removed          *Fig. 3*
                              New Link

BEFORE INTERROGATION          AFTER INTERROGATION

Link                          Link Removed                *Fig. 4*

BEFORE INTERROGATION          AFTER INTERROGATION

Link                          Link Confirmed              *Fig. 5*

LEGEND

- - - - Non-Validated Link or User Added Link
◯ Validated Device
⋰⋱ Non-Validated Device
——— Validated Link

BEFORE INTERROGATION      AFTER INTERROGATION

*Fig. 6*

BEFORE INTERROGATION      AFTER INTERROGATION

*Fig. 7*

BEFORE INTERROGATION      AFTER INTERROGATION

MERGING NETWORK DATA SETS COMPRISING DATA ACQUIRED BY INTERROGATION OF A NETWORK

BACKGROUND OF THE INVENTION

The present invention relates to merging network databases. Network databases are used in supervising a network, that is a network of electronic devices comprising, for example, workstations, personal computers, servers, hubs, routers, bridges, switches, (hereinafter referred to as devices of the network), and links between these devices which may be in the form of physical cable or wireless links. The network may be a local area network (LAN), wide area network (WAN) or other types and may operate in accordance with any desired protocol.

After such a network has been installed, it is desirable for the person appointed network manager to be able to understand the technical operation of the network. In known network management systems, the manner in which the relevant data is retrieved from the managed devices, compiled and displayed has been problematic in several respects. Firstly, the data received from each of the managed devices is simply compiled and displayed as a list of data for the user to interpret. Secondly, the data does not provide information about unmanaged devices. Thirdly, information about a given network device, such as the type of device, location of the device on the network and operating speed of the device, may be contained in different sections of the compiled data. Consequently, conventional systems are cumbersome and difficult to use.

In co-pending UK patent applications numbers 9910843.3, 9910844.1, 9910845.8, 9910838.3, 9910837.5, 9910839.1, 9910840.9, 9910962.1 (each in the name of the assignee of the present application) which are incorporated herein, we describe various arrangements for providing automatic interrogation of the network to thereby produce a network map which may be displayed on a visual display unit showing the devices and links between the devices a data set with details of the network and devices. At its simplest, and where the device is a "managed" device, this interrogation uses a known protocol, such as the SNMP protocol, of the so-called 'agent' of each device which stores the devices unique MAC address, data relating to the type of device and the MAC addresses of the devices which are connected to the ports directly or indirectly.

Once this information is ascertained, it may be stored, for example, on the network manager's work station and used for various purposes. Interrogation of all the devices in the network will usually be carried out relatively infrequently.

Between these interrogations, there may be changes to the physical network itself or to the data set. For example, the network manager using his own knowledge may have manually added to the network data set non-managed devices which cannot be interrogated in the same way as managed devices, and may also have manually inserted known links between devices. Furthermore, devices and links may have been altered (ie added, removed, moved, increased or decreased in capacity). Over the course of time, therefore, the network data set may change substantially from its generation by the previous interrogation of the network.

At a later date, it may desired to interrogate the network again to verify or extend the network data set, and unless all of the earlier information is to be discarded, it is desirable to provide a system to deal with the differences between the newly generated (second) network data set, and the (first) network data set which the network manager already has. In particular, it is desirable not to discard information in the first data set which cannot be shown to be incorrect or not present (eg the information manually added by the network manager). Whilst the network manager can consider each device and link individually and compare them from the two network data sets, and make a decision, it is clearly desirable to be able to produce some kind of system or algorithm to enable the comparison to be carried out by means, for example, of a program running an algorithm on the network manager's computer.

Thus in general terms, the present invention relates to merging one set of data representing a network, into another set of data representing the same network, but that was constructed at a different time to the first data set. The problem to be resolved is how to deal with the similarities and differences between the two sets of data.

SUMMARY OF THE INVENTION

The present invention relates to merging network databases.

The present invention provides a method for providing a data set relating to a network by merging a first data set relating to the network at a first time and a second data set relating to the network at a second, later, time, said first data set comprising data acquired by interrogation of the network and other data, and said second data set comprising data acquired by interrogation of the network, said method comprising:

comparing the data in the first data set with the second data set, and updating the first data set to include additional data present in the second data set which is not present in the first data set.

In this way the information, usually the information which has been added by the network manager subsequent to the initial interrogation of the network, is preserved in creating the new data set.

Furthermore, said updating step may include the step of deleting from the first data set that data where the second data set includes information that the aspect that said data relates to is no longer present in the network.

By this method step, information which has changed and is incorrect is deleted from the first data set.

The present invention also provides a computer program on a computer readable medium or embodied in a carrier wave for use in providing a data set relating to a network by merging a first data set relating to the network at a first time and a second data set relating to the network at a second, later, time, said first data set comprising data acquired by interrogation of the network and other data, and said second data set comprising data acquired by interrogation of the network, said program comprising:

program means for comparing the data in the first data set with the second data set, and program means for updating the first data set to include additional data present in the second data set which is not present in the first data set.

A preferred embodiment of the invention will now be described by way of example and with reference to the accompanying drawings in which.

DESCRIPTION OF THE PREFERRED EMBODIMENTS

Figure 1:
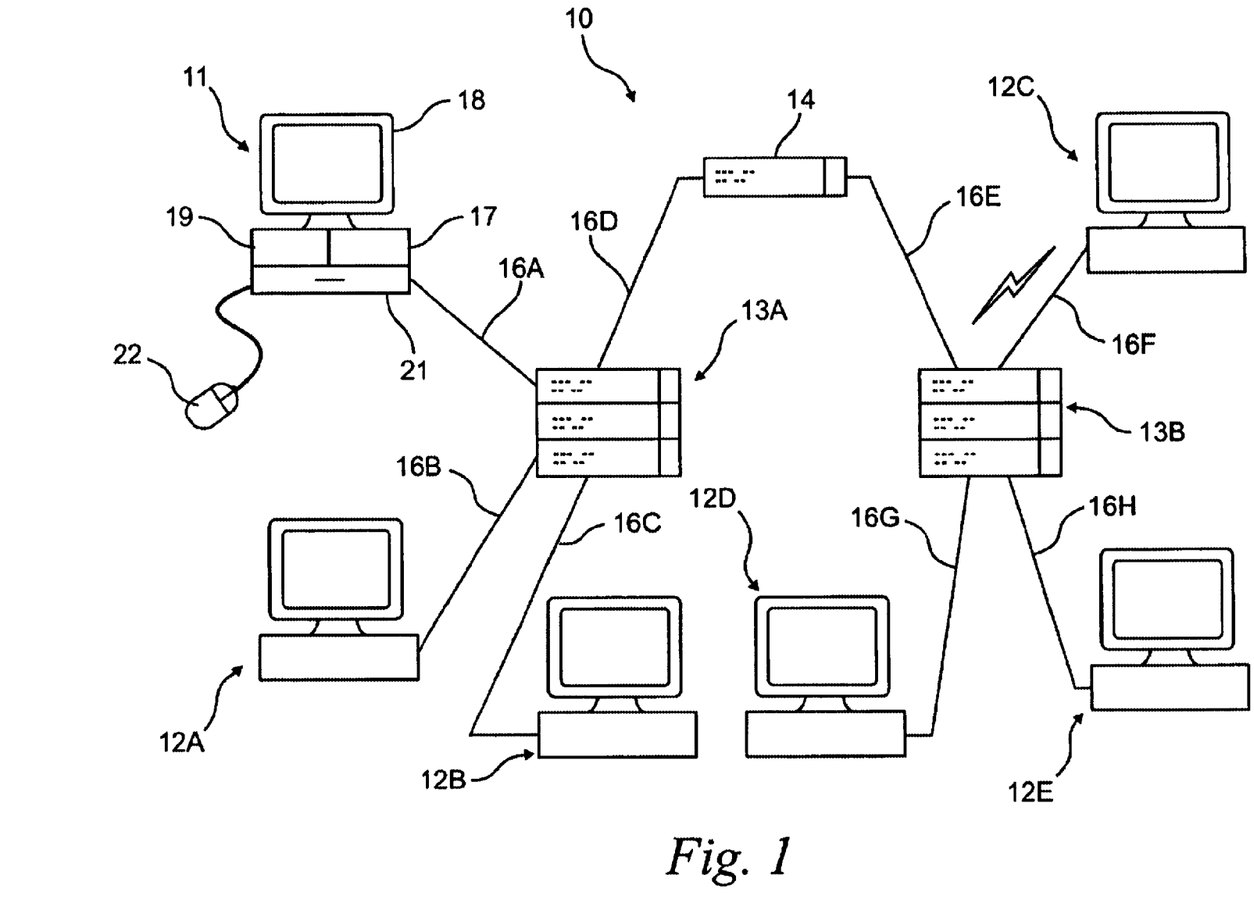
FIG. 1 is a diagrammatic view of a network incorporating a preferred embodiment of the invention.

Referring to FIG. 1 there is shown a network 10 comprising a plurality of devices in the form of a network supervisor's workstation or computer 11, other workstations 12B–E, hubs 13A, 13B, and switch 14. The network is a simple network and is set out for purposes of illustration only. Other configurations and arrangements, may be used.

The devices are connected together by means of links 16A–H which may be hard wired and utilise any desired protocol, and link 16F which is a wireless link.

The network supervisor's workstation includes, in addition to a visual display unit 18, a central processing unit or signal processor 19, a selector which may be in the form of a mouse 22, a program store 21 which may comprise, for example, a CD drive, a floppy disk drive or a zip drive, and a memory 17 for storing a program which may have been loaded from the program store 21 or downloaded for example via Internet from a website.

By means which is disclosed in the co-pending patent applications referred to above, the network supervisor's computer 11 may interrogate and analyse the network, and store in the memory 17 the information relating to the devices within the network and the links between the devices. In essence, most quality devices include a so-called agent which stores information about the device such as its unique MAC number, its ID which identifies what the device is and what model type it is, how many ports it has and how they are connected, and the address to which at least some of the ports are connected. The computer 11 interrogates the agents of each device.

The information obtained by the interrogation at a first time is stored on the network supervisor's computer in the form of a first data set. This first data set will initially only include the information obtained by the interrogation but over the subsequent period of time may include further information which the network manager adds to the data set. For example, the network manager may add information relating to non-managed devices including their links to the managed devices.

This information will comprise a first data set which includes information relating to not only the devices and links between them, but also parts of the devices, for example, units or ports (defined hereafter) and combinations of devices defined as subnets, and multinets, (which are defined hereafter).

The computer 11 may, on command from the selector 22, process signals from the memory 17 by the signal processor 19 and provide on the visual display unit 18 a network map showing each of the devices and the links therebetween.

Definitions:

| | | |
|---|---|---|
| Object | = | Multinet, Subnet, Node, Unit, Port, Link |
| Multinet | = | A group of subnets which may be linked to the remainder of the network or other multinets by means of a single switch or router |
| Subnet | = | A group of nodes and links which may be, for example, linked to the remainder of the network through a single switch or router |
| Node | = | A device connected in the network |
| Unit | = | A module or blade in a stack or chassis of a device |
| Port | = | A physical connector on a networked device to which a connection can be made |
| Link | = | A connection between two nodes |
| Discovery | = | The method used to determine details of multinet, subnet and which nodes are in each subnet |
| Sizing | = | The method used to determine the unit and port details on a device |
| Topology | = | The method used to determine details of the links between nodes |

Figure 2:
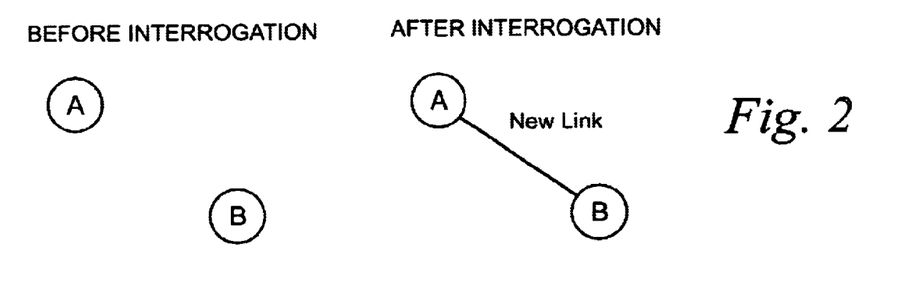
FIGS. 2 to 8 show a series of possible links between ports of two network devices, the left part of each drawing showing the link established in a first set of data representing a network (ie the first network map) and the right part of each drawing showing the link detected during later interrogation to produce a second, later, network map.

Particular problems which need to be solved in merging two data sets on networks include:

i) Identifying objects in both sets of data, that represent the same 'real' object in the network, given that the 'real' object may change over time. Such objects include network devices, links between network devices, subnets, etc.

ii) Ensuring that objects manually added to the first data set by the user, do not get removed when merging or creating in the new set of data.

iii) Handling objects that move from one part of the network to another over time (eg between subsets)

iv) Handling changes in a network device's configuration, eg changing IP addresses, objects added/removed, etc As examples of how the problems may be solved, we refer to FIG. 2 in which the left drawing shows two devices A, B. As with all of FIGS. 2 to 8, the left drawing shows the network plan deduced from the original first network data set and the right drawing shows the network plan deduced by the new interrogation of the objects to form the second network data set. Thus in the original network plan, devices A and B are not connected, and after interrogation, in the new plan, devices A and B appear to be connected by a link and so in the final produced network plan, that link will be added between devices A and B. A new ID is provided.

Figure 3:
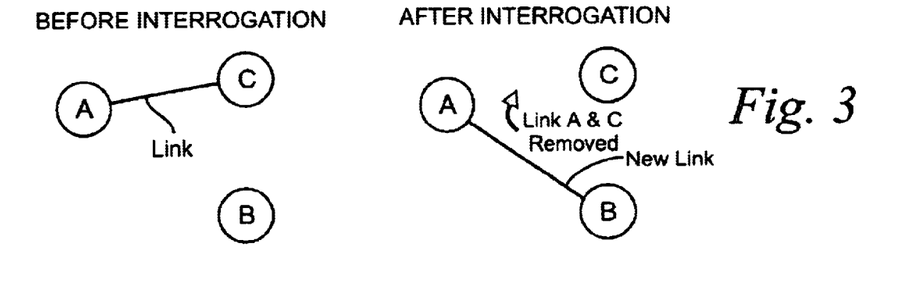

Referring to FIG. 3, there are shown three devices A, B and C, and in the original network plan devices A and C are interconnected, and when the system is interrogated to produce the new network plan, it is deduced that devices A and C are interconnected. In this case, in the new plan, the new link is added from A to B, and the link from A to C is removed because there is port conflict. However it is necessary to check the addresses (nodes) provided at all of the devices A, B and C to ensure the veracity of the arrangement shown in the right half of FIG. 3. The arrangement shown in the right half of FIG. 3 is then added to the network map.

Figure 4:
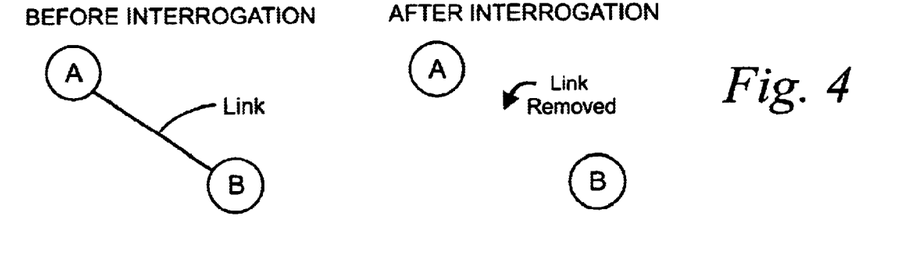

In the arrangement of FIG. 4, in the original network map there is a link between devices A and B. When interrogated again, there does not appear to be a link and so this is removed.

Figure 5:
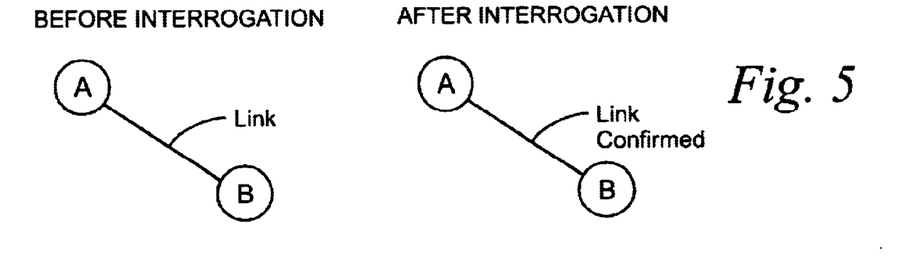

In FIG. 5, there is a link in the original network map between devices A and B, and that link is confirmed in the interrogation for the new network map, and so the link remains and the existing identity (ID) is maintained.

Figure 6:
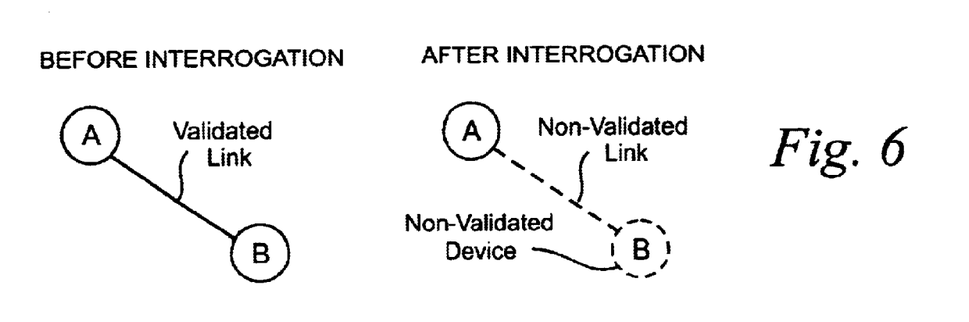

In FIG. 6, the original network map has a link between devices A and B but on interrogation device B cannot be found (it may be present but not switched on, for example). It is thus retained as a non-validated link and device.

Figure 7:
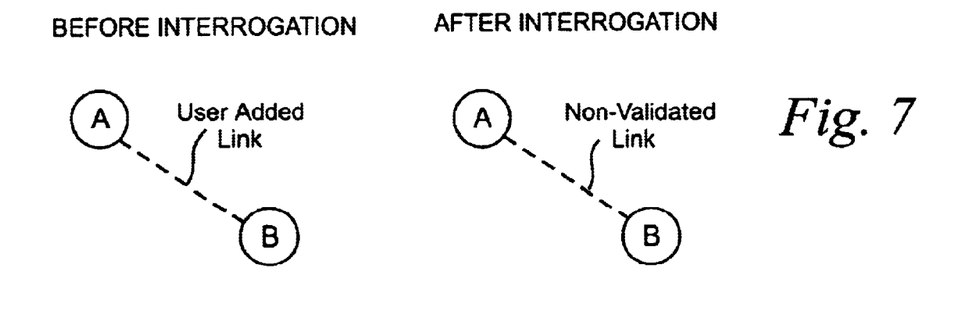

In FIG. 7, the original network map has a user added link between devices A and B, and this is retained in the new network map. There is no way of determining whether that link is or is not present by the interrogation method employed and so one retains the relevant unverified link.

In FIG. 8, once again the original map has a user added link between devices A and B, but in the new interrogation process, a link is established between A and B and so that link is turned into a validated link, that is, a non-user addition.

FIGS. 2 to 8 relate to the problems to be overcome in relation to different link arrangements between the first data set and the second data set. There will be similar problems to be overcome in relation to multinets, subnets, nodes, units and ports which will need to be addressed in the same or similar manner.

Figure 9:
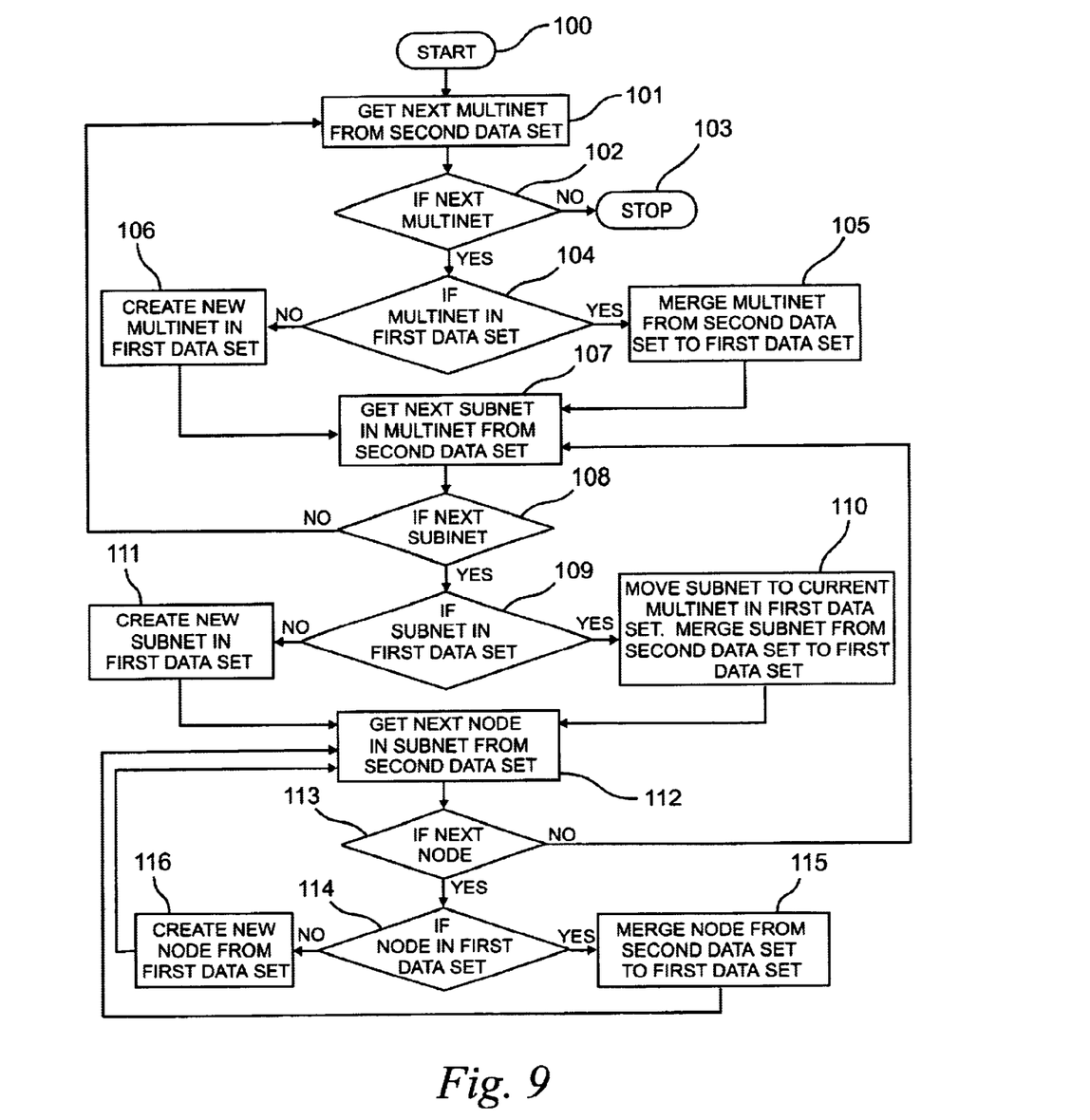
FIG. 9 is a flow chart for merging discovery data.
Figure 10:
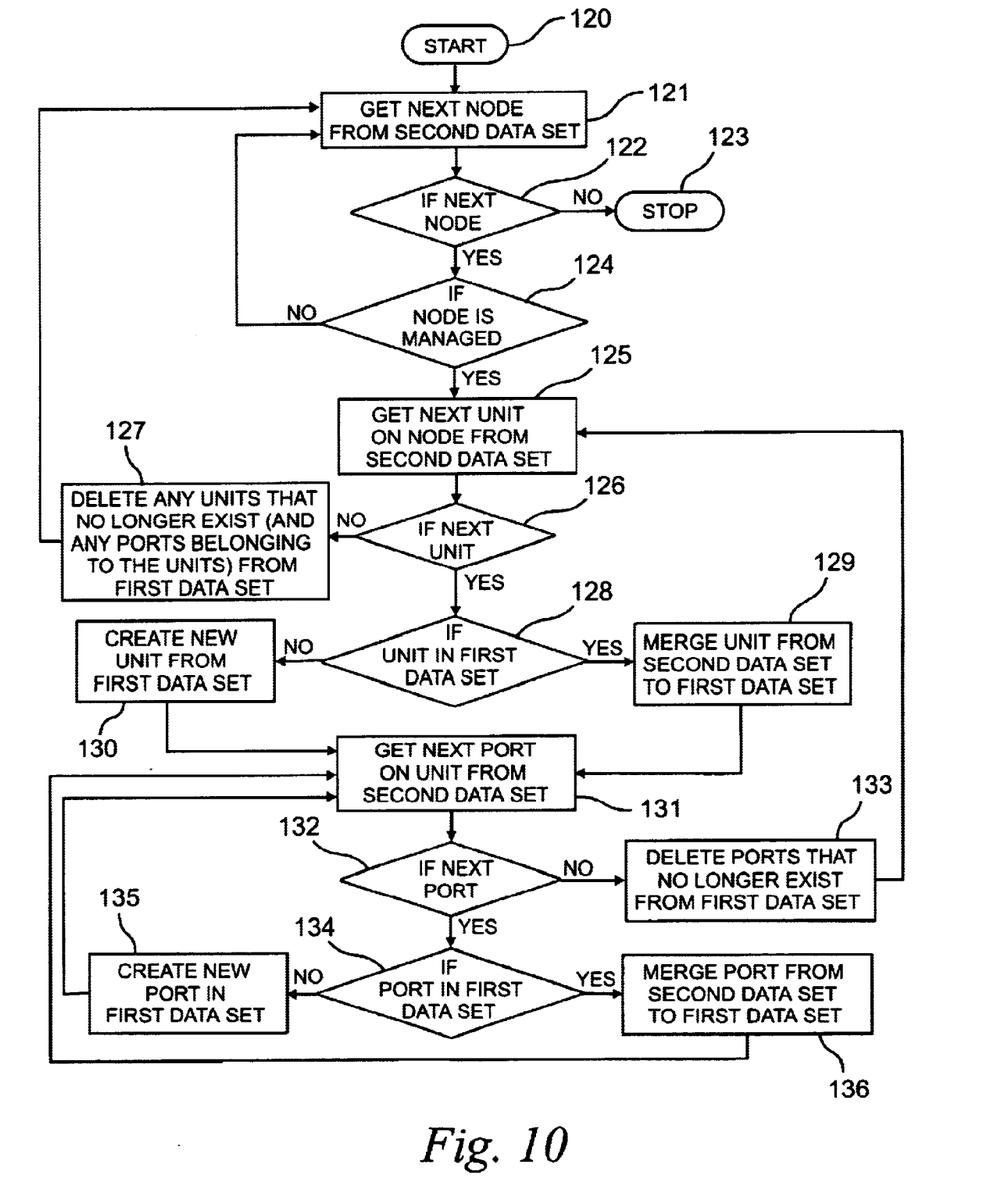
FIG. 10 is a flow chart for merging sizing data.
Figure 11:
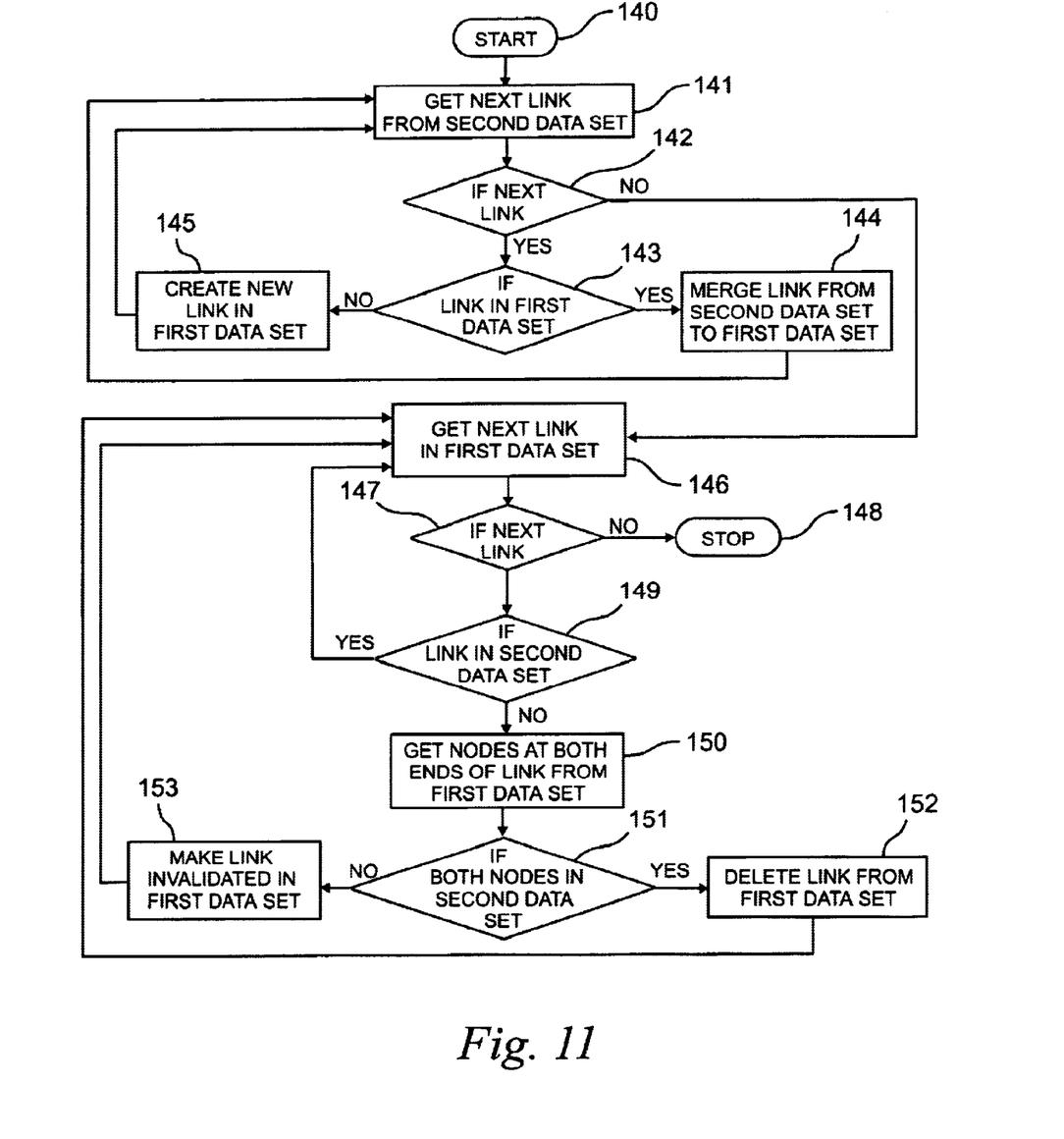
FIG. 11 is a flow chart for merging topology data.

The flow diagrams in FIGS. 9, 10, 11, outline the merge processes which provide the solutions set out in FIGS. 2 to 7 as will be set out hereafter. FIGS. 9, 10, 11 deal with respectively Discovery, Sizing and Topology information. For all three processes, specific match criteria have been defined for each of the object types involved, so that objects in both databases that represent the same 'real' object in the network can be identified. Subsequently this allows the process to determine whether:

a) a new object must be created (as it currently doesn't exist in the first data set), or b) an existing object needs to be modified (as it does already exist in the first data set but has changed over time as found in the second data set), or c) an object needs to be removed (as it does exist in the first data set, but conflicts with information in the second data set).

Note that node objects are not removed from the first data set, if they do not exist in the second data set, as there is no way of determining whether or not the said node no longer exists on the network, or is temporarily not responding.

The match criteria used by the Discovery Merge process (shown in FIG. 9) to identify similar objects in both data sets, is as follows:

| | | |
|---|---|---|
| Multinet Match Criteria (used, for example, in step 104) | = | the multinets must contain one or more of the same subnets (refer to Subnet match criteria) |
| Subnet Match Criteria (used, for example, in step 109) | = | the subnets must have the same subnet IP address and use the same subnet mask |
| Node Match Criteria (used, for example, in step 114) | = | the nodes must have one or more MAC addresses that are the same. |

The match criteria used by the Sizing Merge process (shown in FIG. 10) to identify similar objects in both data sets, is as follows:

| | | |
|---|---|---|
| Unit Match Criteria (used, for example in step 128) | = | i) the units must be on the same Node (refer to Node Match Criteria). ii) the units must have the same unit number. |
| Port Match Criteria (used, for example, in step 134) | = | i) the ports must be on the same Node (refer to Node Match Criteria) ii) the ports must be on the same Unit (refer to Unit Match Criteria). iii) the port must have the same port number. |

The match criteria used by the Topology Merge process (shown in FIG. 11) to identify similar objects in both data sets, is as follows:

| | | |
|---|---|---|
| Link Match Criteria (used, for example, in steps 143 and 149) | = | the link must connect the same two nodes (refer to Node Match Criteria) |

Note that the above algorithm could be applied to any type of network, e.g. IP, IPX.

It may be noted that the process of deduction set out in FIG. 2 is derived from, for example, step 145 of FIG. 11.

The process of addition of a new link between A and B as set out in FIG. 3 is also provided by step 145.

The process of deletion of the link between A and C as set out in FIG. 3 is provided by the step 152.

The process as set out in FIG. 4 is provided by step 152.

Figure 8:
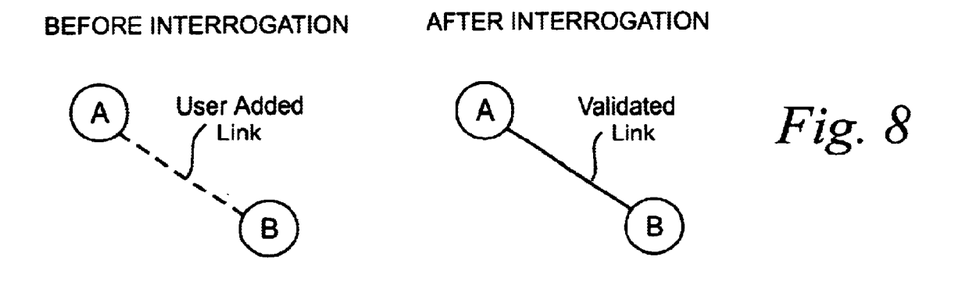

The process as set out in FIG. 6 is provided by step 143 of FIG. 11, and the process set out in FIG. 8 is provided by step 143.

We have described how the network may be supervised. The method of the invention may be carried out under the control of the network supervisor's workstation or computer and in particular by means of a program controlling the processor apparatus of that computer or elsewhere in the system.

The program for controlling the operation of the invention may be provided on a computer readable medium, such as a CD, or a floppy disk, or a zip drive disk carrying the program or their equivalent, or may be provided on a computer or computer memory carrying the website of, for example, the supplier of the network products. The program may be downloaded from whichever appropriate source via, for example, a telephone line, a wireless radio, or an infra-red link, in each of which case it may be embodied in a carrier wave and used to control the processor to carry out the steps of the invention as described.

The program includes steps corresponding to all of the steps set out in FIGS. 9, 10 and 11, in particular steps 100 to 116 of FIG. 9, 120 to 136 of FIG. 10, and 140 to 152 of FIG. 11.

The steps shown in FIG. 9 are as follows:

Step 100 Start

Step 101 Get next multinet from second data set

Step 102 Is that multinet the next multinet? If no, go to step 103, if yes, go to step 104.

Step 103 Stop

Step 104 Is that multinet in the first data set? If yes, go to step 105, if no, go to step 106.

Step 105 Update multinet from second data set to first data set and go to step 107.

Step 106 Create a new multinet in the first data set and go to step 107.

Step 107 Get the next subnet in the relevant multinet from the second data set.

Step 108 Is that subnet the next subnet? If yes, go to step 109, if no, return to step 101.

Step 109 Is the subnet in the first data set. If yes, go to step 110, if no, go to step 111.

Step 110 Move the subnet to the current multinet in the first data set. Update the subnet from second data set to first data set and go to step 112.

Step 111 Create new subnet in first data set.

Step 112 Get next node in subnet from second data set.

Step 113 Is the node the next node? If no, return to step 107, if yes, go to step 114.

Step 114 Is the node in first data set? If yes, proceed to step 115, if no, go to step 116.

Step 115 Update node from second data set to first data set and return to step 112.

Step 116 Create new node in first data set and return to step 112.

The steps shown in FIG. 10 are as follows:

Step 120 Start
Step 121 Get next node from second data set
Step 122 Is the node the next node? If no, go to step 123, if yes, go to step 124.
Step 123 Stop
Step 124 Is the node managed? If no, return to step 121, if yes, go to step 125.
Step 125 Get the next unit on node from the second data set.
Step 126 Is the unit the next unit? If no, go to step 127, if yes, go to step 128.
Step 127 Delete any units that no longer exist and any ports belonging to the units from the first data set and go to step 121.
Step 128 Is the unit in the first data set? If yes, go to step 129, if no, go to step 130.
Step 129 Update unit from second data set to first data set and go to step 131.
Step 130 Create new unit in first data set and go to step 131.
Step 131 Get the next port on the unit from second data set.
Step 132 Is the port the next port? If no go to step 133, if yes, go to step 134.
Step 133 Delete ports that no longer exist from the first data set and return to step 125.
Step 134 Is the port in first data set? If no, go to step 135, if yes, go to step 136.
Step 135 Create a new port in the first data set and return to step 131.
Step 136 Merge port from second data set to first data set and return to step 131.

The steps shown in FIG. 11 are as follows:

Step 140 Start
Step 141 Get next link from second data set
Step 142 Is the link the next link? If yes, go to step 143, if no, go to step 146.
Step 143 Is the link in the first data set? If yes, go to step 144, if no, go to step 145.
Step 144 Merge link from second data set to first data set and return to step 141.
Step 145 Create new link in first data set and return to step 141.
Step 146 Get the next link in the first data set.
Step 147 Is the link the next link? If no, go to step 148, if yes, go to step 149.
Step 148 Stop.
Step 149 Is the link in the second data set? If yes, return to step 146, if no, go to step 150.
Step 150 Get nodes at both ends of link from first data set.
Step 151 Are both nodes in second data set? If yes, go to step 152, if no, go to step 153.
Step 152 Delete link from first data set and return to step 146.
Step 153 Make link invalidated in first data set and return to step 146.

The invention is not restricted to the details of the foregoing example.

What is claimed is:

1. In a network of devices, a method of managing the network, including:
    at a first time, interrogating agents of managed devices within the network to provide a first data set relating to the network,
    at a second, later, time, interrogating the agents of managed devices within the network to provide a second data set relating to the network,
    updating the first data set in accordance with a predetermined set of rules by merging the first data and the second data set, to deduce changes in the network, said updating step including:
        comparing the data in the first data set with the second data set to determine additional data present in the second data set which is not present in the first data set, the data in the first data set comprising discovery data, topology data, and sizing data, and
        updating the first data set to include the additional data present in the second data set which is not present in the first data set.

2. A method as claimed in claim 1 wherein said updating step includes the step of deleting from the first data set that data where the second data set includes information that the aspect that said data relates to is no long present in the network.

3. A method as claimed in claim 1 wherein said updating step includes the step of creating new data in the first data set where additional data is present in the second set which is not present in the first set.

4. A method as claimed in claim 1 wherein said updating step includes the step of modifying new data in the first data set where additional data is present in the second set which is not present in the first set.

5. A method as claimed in claim 1 including an initial step of interrogation of the network at the second time to provide said second data set.

6. A method as claimed in claim 1 wherein said data includes data relating to the multinet or multinets of the network.

7. A method as claimed in claim 1 wherein said data includes data relating to the subnet or subnets of the network.

8. A method as claimed in claim 1 wherein said data includes data relating to the node or nodes of the network.

9. A method as claimed in claim 1 wherein said data includes data relating to the unit or units of the network.

10. A method as claimed in claim 1 wherein said data includes data relating to the port or ports of the network.

11. A computer program on a computer readable medium, said computer program comprising software for performing the method of claim 1.

12. A computer program on a computer readable medium for use in managing a network of devices comprising:
    program means for interrogating agents of managed devices within the network at a first time to provide a first data set relating to the network,
    program means for interrogating agents of managed devices within the network at a second, later, time to provide a second data set relating to the network,
    program means for updating the first data set in accordance with a predetermined set of rules by merging the first data and the second data set, to deduce changes in the network, said updating step including comparing the data in the first data set with the second data set to determine additional data present in the second data set which is not present in the first data set, the data in the first data set comprising discovery data, topology data, and sizing data, and
    program means for updating the first data set to include the additional data present in the second data set which is not present in the first data set.

13. A computer program as claimed in claim 12 wherein said program means for updating step includes program means for deleting from the first data set that data where the second data set includes information that the aspect that said data relates to is no long present in the network.

14. A computer program as claimed in claim 12 wherein said data includes data relating to the multinet or multinets of the network.

15. A computer program as claimed in claim 12 wherein said data includes data relating to the subnet or subnets of the network.

16. A computer program as claimed in claim 12 wherein said data includes data relating to the node or nodes of the network.

17. A computer program as claimed in claim 12 wherein said data includes data relating to the unit or units of the network.

18. A computer program as claimed in claim 12 wherein said data includes data relating to the port or ports of the network.

19. A network comprising a computer including a program as claimed in claim 12.

20. A computer program embodied in a carrier wave for use in managing a network of devices comprising:
    program means for interrogating agents of managed devices within the network at a first time to provide a first data set relating to the network,
    program means for interrogating agents of managed devices within the network at a second, later, time to provide a second data set relating to the network,
    program means for updating the first data set in accordance with a predetermined set of rules by merging the first data and the second data set, to deduce changes in the network, said updating step including comparing the data in the first data set with the second data set to determine additional data present in the second data set which is not present in the first data set, the data in the first data set comprising discovery data, topology data, and sizing data, and
    program means for updating the first data set to include the additional data present in the second data set which is not present in the first data set.

21. A computer program as claimed in claim 20 wherein said program means for updating step includes program means for deleting from the first data set that data where the second data set includes information that the aspect that said data relates to is no long present in the network.

22. A computer program as claimed in claim 20 wherein said data includes data relating to the multinet or multinets of the network.

23. A computer program as claimed in claim 20 wherein said data includes data relating to the subnet or subnets of the network.

24. A computer program as claimed in claim 20 wherein said data includes data relating to the node or nodes of the network.

25. A computer program as claimed in claim 20 wherein said data includes data relating to the unit or units of the network.

26. A computer program as claimed in claim 20 wherein said data includes data relating to the port or ports of the network.

27. In a network of devices, a method of managing the network, including:
    at a first time, interrogating agents of managed devices within the network to provide a first data set relating to the network, said first data set comprising first discovery data;
    at a second, later, time, interrogating the agents of managed devices within the network to provide a second data set relating to the network, said second data set comprising second discovery data;
    determining whether a first multinet in the first data set matches a second multinet in the second data set;
    if the first multinet in the first data set matches the second multinet in the second data set, then merging the second multinet into the first data set; and
    if the first multinet in the first data set does not match the second multinet in the second data set, then creating a new multinet in the first data set.

28. The method of claim 27, further comprising:
    determining whether a first subnet in the first data set matches a second subnet in the second data set, the second subnet being on the second multinet;
    if the first subnet in the first data set matches the second subnet in the second data set, then merging the second subnet into the first data set; and
    if the first subnet in the first data set does not match the second subnet in the second data set, then creating a new subnet in the first data set.

29. The method of claim 28, further comprising:
    determining whether a first node in the first data set matches a second node in the second data set, the second node being on the second subnet;
    if the first node in the first data set matches the second node in the second data set, then merging the second node into the first data set; and
    if the first node in the first data set does not match the second node in the second data set, then creating a new node in the first data set.

30. The method of claim 27, wherein determining whether the first multinet in the first data set matches the second multinet in the second data set comprises determining whether the first multinet and the second multinet have at least one same subnet.

31. The method of claim 28, wherein determining whether the first subnet in the first data set matches the second subnet in the second data set comprises determining whether the first subnet and the second subnet have a same subnet IP address and a same subnet mask.

32. The method of claim 29, wherein determining whether the first node in the first data set matches the second node in the second data set comprises determining whether the first node and the second node have at least one same MAC address.

33. In a network of devices, a method of managing the network, including:
    at a first time, interrogating agents of managed devices within the network to provide a first data set relating to the network, said first data set comprising first sizing data;
    at a second, later, time, interrogating the agents of managed devices within the network to provide a second data set relating to the network, said second data set comprising second sizing data;
    determining whether a first unit in the first data set matches a second unit in the second data set, the second unit being on a node that is managed;
    if the first unit in the first data set matches the second unit in the second data set, then merging the second unit into the first data set; and
    if the first unit in the first data set does not match the second unit in the second data set, then creating a new unit in the first data set.

34. The method of claim 33, further comprising:
    determining whether a first port in the first data set matches a second port in the second data set, the second port being on the second unit;

if the first port in the first data set matches the second port in the second data set, then merging the second port into the first data set; and if the first port in the first data set does not match the second port in the second data set, then creating a new port in the first data set.

35. The method of claim 33, wherein determining whether the first unit in the first data set matches the second unit in the second data set comprises determining (i) whether the first unit and the second unit are on a same node; and (ii) whether the first unit and the second unit have a same unit number.

36. The method of claim 33, wherein determining whether the first port in the first data set matches the second port in the second data set comprises determining (i) whether the first port and the second port are on a same node and a same unit; and (ii) whether the first port and the second port have a same port number.

37. The method of claim 1, (i) wherein comparing the data in the first data set with the second data set comprises making a determination of whether a first link in the first data set matches a second link in the second data set; and (ii) wherein updating the first data set to include the additional data present in the second data set comprises merging the second link in the second data set into the first data set based on the determination that the first link in the first data set matches the second link in the second data set.

38. In a network of devices, a method of managing the network, including:
  at a first time, interrogating agents of managed devices within the network to provide a first data set relating to the network, said first data set comprising first topology data;
  at a second, later, time, interrogating the agents of managed devices within the network to provide a second data set relating to the network, said second data set comprising second topology data;
  making a first determination of whether a link in the first data set is present in the second data set;
  based on the first determination that the link in the first data set is not present in the second data set, then making a second determination of whether nodes of the link are in the second data set;
  based on the second determination that the nodes of the link are present in the second data set, then deleting the link in the first data set; and
  based on the second determination that the nodes in the first data set are not present in the second data set, then invalidating the link in the first data set.

39. The method of claim 38, wherein the first determination of whether the link in the first data set is present in the second data set comprises determining whether the link connects same nodes.

40. The method of claim 1, wherein the data comprises information on non-managed devices.

41. The method of claim 12, wherein the data comprises information on non-managed devices.

42. The method of claim 20, wherein the data comprises information on non-managed devices.

* * * * *